(12) United States Patent
Yamazaki et al.

(10) Patent No.: US 6,694,182 B1
(45) Date of Patent: Feb. 17, 2004

(54) WEARABLE CALORIE CALCULATOR

(75) Inventors: Iwao Yamazaki, Tokyo (JP); Kimiyo Yamazaki, Tokyo (JP)

(73) Assignee: Ya-Man Ltd., Tokyo (JP)

( * ) Notice: Subject to any disclaimer, the term of this patent is extended or adjusted under 35 U.S.C. 154(b) by 0 days.

(21) Appl. No.: 10/148,169

(22) PCT Filed: Feb. 2, 2000

(86) PCT No.: PCT/JP00/00565

§ 371 (c)(1),
(2), (4) Date: May 31, 2002

(87) PCT Pub. No.: WO01/41645

PCT Pub. Date: Jun. 14, 2001

(30) Foreign Application Priority Data

Dec. 7, 1999 (JP) .......................... 11/347174

(51) Int. Cl.$^7$ ................................ A61B 5/05
(52) U.S. Cl. ..................................... 600/547
(58) Field of Search ................... 600/547, 301, 600/503, 549, 587, 300; 702/131

(56) References Cited

U.S. PATENT DOCUMENTS 5,788,655 A * 8/1998 Yoshimura et al. ......... 600/587
6,030,342 A * 2/2000 Amano et al. ............. 600/301

FOREIGN PATENT DOCUMENTS

JP 02002355230 A * 12/2002

* cited by examiner

*Primary Examiner*—Max F. Hindenburg
*Assistant Examiner*—Brian Szmal
(74) *Attorney, Agent, or Firm*—Jones, Tullar & Cooper, P.C.

(57) ABSTRACT

Disclosed is an improved wearable calorie calculator, which takes the degree of active strength and the quantity of basal metabolism into account to calculate the total number of calories consumed each day with precision, and which visually informs the wearer of the goal or outcome of exercises. The calorie calculator comprises: a housing 1 having a display D equipped therewith, the housing 1 being wearable to a selected part of one's body; electrodes E1 and E2 for determining bioelectric impedance; momentum gauge means 190 responsive to three-dimensional body movements for determining the momentum of a wearer; cardiac rate measuring means 210; individual data inputting means 120; body fat percentage calculator means 130; basal metabolism calculator means 140; a daily consumption calorie calculator means 220; whereby at least the body fat percentage and the total number of calories consumed a day are given on the display D.

16 Claims, 6 Drawing Sheets

WEARABLE CALORIE CALCULATOR

TECHNICAL FIELD

The present invention relates to a wearable calorie calculator capable of calculating the number of calories a wearer consumes each day from all-day movements on the basis of his momentum and cardiac rate etc.

BACKGROUND ART

A conventional calorie calculator has a pedometer or an accelerator gauge built therein, so that the number of calories a wearer consumes may be determined in terms of the number of step or of the walking speed. The calculator, however, cannot determine the number of calorie the wearer consumes with accuracy; because it does not take the loading factor (for example, how much the wearer is loaded when climbing a steep slope) into account.

An improved calculator uses the interrelation between the cardiac rate and the number of calories to calculate the number of calories the wearer consumes in terms of measured cardiac rates. The interrelation between the cardiac rate and the number of calories consumed, however, is dependent on different physical conditions of the wearer. Specifically such interrelation is substantially different between the active condition and non-active condition. Therefore, this type of calorie calculator is equipped with an accelerator for determining in which condition the wearer is, active or non-active condition.

However, assuming that the wearer rides on a vehicle in non-active condition, the acceleration gauge erroneously realizes that he is in active state.

Also, the interrelation between the cardiac rate and the number of calories consumed varies with the degree of active strength in movement. It is quite different between walking and running. For these reasons calculation of the number of calories consumed relying on the interrelation between the cardiac rate and the number of calories is inevitably inaccurate.

Incidentally, the total number of calories consumed a day is usually calculated by adding the number of calories consumed by all-day movements and exercises unavoidable in daily life to the amount of basal metabolism necessary for maintaining life. The number of calories consumed by all-day movements and exercises, that is, the momentum, can be calculated by multiplying the degree of active strength by the length of time taken for the exercise.

The degree of active strength is estimated to be 2.0 for a practice of walking, 7.0 for a practice of running ad such like. Specifically it is given by determining how many times of calories consumed for the basal metabolism is necessary for a particular exercise or movement. The multiplying factor is called "energy metabolism coefficient". As may be realized, the total number of calories consumed a day should be naturally calculated on the basis of the basal metabolism.

The basal metabolism is a primary amount of energy consumed in bodies, and it is dependent on age or weight: energy is consumed in muscle, and accordingly the basal metabolism will increase with increase of muscle.

As the muscle decreases, the part of body where energy is consumed decreases, and accordingly the basal metabolism decreases, resulting in the pyknic body.

The basal metabolism varies proportionally with the amount of muscle, and therefore, the exact basal metabolism can be determined in terms of the sex, age, height, weight and the fat-free weight representing the amount of muscle, which can be obtained by subtracting the body fat from the weight. This necessitates measurement of bioelectric impedance from which the body fat percentage can be calculated.

The conventional calorie meters lack the function of measuring the body fat percentage, and therefore, they are incapable of distinguishing fat people from muscular people. In short, such conventional calorie meters calculate the number of calories consumed by exercise irrespective of the basal metabolism being dependent on the amount of muscle.

Also, disadvantageously such conventional calorie meters can display the cardiac rate and the number of calories consumed a day, but they cannot provide any pieces of information permitting the user to set the goal for exercise or to make a decision as to whether the current momentum is appropriate for the purpose.

Therefore, users are apt to quickly lose interest in such calorie meters and stop using them soon without having gained much advantage.

One object of the present invention is to provide a wearable calorie calculator taking into account the fact of the quantity of basal metabolism being dependent on the body fat percentage, the calorie calculator being capable of calculating the total number of calories consumed per day with accuracy thanks to consideration both of such fact and different degrees of active strength in movement; and at the same time, permitting users to set their goals and realize the outcomes of exercises actually taken.

DISCLOSURE OF INVENTION

The present invention is constructed as described below.

A calorie calculator according to claim 1 of the present invention comprises: a housing having a display equipped therewith, said housing being wearable to a selected part of one's body; electrodes attached to the surface of the housing for determining bioelectric impedance; momentum gauge means responsive to three-dimensional body movements for determining the momentum of a wearer; cardiac rate measuring means; individual data inputting means for inputting the sex, age, height, weight and other personal data; body fat percentage calculator means for determining the body fat percentage of the wearer from the bioelectric impedance and personal data; basal metabolism calculator means for determining the quantity of basal metabolism of the wearer from the body fat percentage and the personal data of the wearer; and calorie calculator means for calculating the total number of calories consumed a day from the momentum, cardiac rate, and quantity of basal metabolism of the wearer, whereby at least the body fat percentage and the total number of calories consumed a day are given on the display.

A calorie calculator according to claim 2 of the present invention comprises: a housing having a display equipped therewith, said housing being wearable to a selected part of one's body; electrodes attached to the surface of the housing for determining bioelectric impedance; momentum gauge means responsive to three-dimensional body movements for determining the momentum of a wearer; cardiac rate measuring means; individual data inputting means for inputting the sex, age, height, weight, and other personal data; body fat percentage calculator means for determining the body fat percentage of the wearer from the bioelectric impedance and personal data; basal metabolism calculator means for determining the quantity of basal metabolism of the wearer from the body fat percentage and personal data of the wearer; tele-body fat percentage setting means for setting a goal at a desired body fat percentage; tele-consumption calorie calculator means for determining the number of calories required for reaching the goal of desired body fat percentage; and calorie calculator means for calculating the total number of calories consumed a day from the momentum, cardiac rate, and basal metabolism of the wearer, whereby at least the total number of calories consumed a day and the number of calories required for reaching the goal are given on the display along with the body fat percentage.

A calorie calculator according to claim 3 of the present invention comprises: a housing having a display equipped therewith, said housing being wearable to a selected part of one's body; electrodes attached to the surface of the housing for determining bioelectric impedance; momentum gauge means responsive to three-dimensional body movements for determining the momentum of a wearer; cardiac rate measuring means; individual data inputting means for inputting the sex, age, height, weight, and other personal data; body fat percentage calculator means for determining the body fat percentage of the wearer from the bioelectric impedance and personal data; basal metabolism calculator means for determining the quantity of basal metabolism of the wearer from the body fat percentage and personal data of the wearer; tele-body fat percentage setting means for setting a goal at a desired body fat percentage; momentum calculator means for determining the momentum required for reaching the goal of desired body fat percentage; and calorie calculator means for calculating the total number of calories consumed a day from the momentum, cardiac rate, and quantity of basal metabolism, whereby at least the body fat percentage, the required momentum, and the total number of calories consumed a day are given on the display.

A calorie calculator according to claim 4 of the present invention comprises: a housing having a display equipped therewith, said housing being wearable to a selected part of one's body; electrodes attached to the surface of the housing for determining bioelectric impedance; momentum gauge means responsive to three-dimensional body movements for determining the momentum of a wearer; cardiac rate measuring means; individual data inputting means for inputting the sex, age, height, weight, and other personal data; body fat percentage calculator means for determining the body fat percentage of the wearer from the bioelectric impedance and personal data; basal metabolism calculator means for determining the quantity of basal metabolism of the wearer from the body fat percentage and personal data of the wearer; tele-body fat percentage setting means for setting a goal at a desired body fat percentage; tele-consumption calorie calculator means for determining the number of calories required for reaching the goal of desired body fat percentage; calorie calculator means for calculating the total number of calories consumed a day from the momentum, cardiac rate, and quantity of basal metabolism; and tele-consumption calorie renewing means for renewing the number of calories required for reaching the goal in consideration of the total number of calories consumed per day, whereby at least the number of required calories renewed by the tele-consumption calorie renewing means are given on the display along with the body fat percentage.

A calorie calculator according to claim 5 as described in claims 1, 2, 3, or 4 of the present invention is characterized in that said momentum gauge means responsive to three-dimensional movements for determining the momentum of a wearer may comprise a quickening gauge for counting moves of the body in three axial directions and for determining the momentum in terms of counts.

A calorie calculator according to claim 6 as described in claims 1, 2, 3, or 4 of the present invention is characterized in that said momentum gauge means responsive to three-dimensional movements for determining the momentum of a wearer may comprise an acceleration gauge for determining the momentum in terms of detected accelerations in three axial directions.

A calorie calculator according to claim 7 as described in claims 1, 2, 3, or 4 of the present invention is characterized in that said momentum gauge means responsive to three-dimensional movements for determining the momentum of a wearer may comprise a quickening gauge for counting moves of the body in three axial directions, and an acceleration gauge for determining accelerations in three axial directions, whereby the momentum may be determined in terms of counts and accelerations.

BEST MODE FOR CARRYING OUT THE INVENTION

Figure 1:
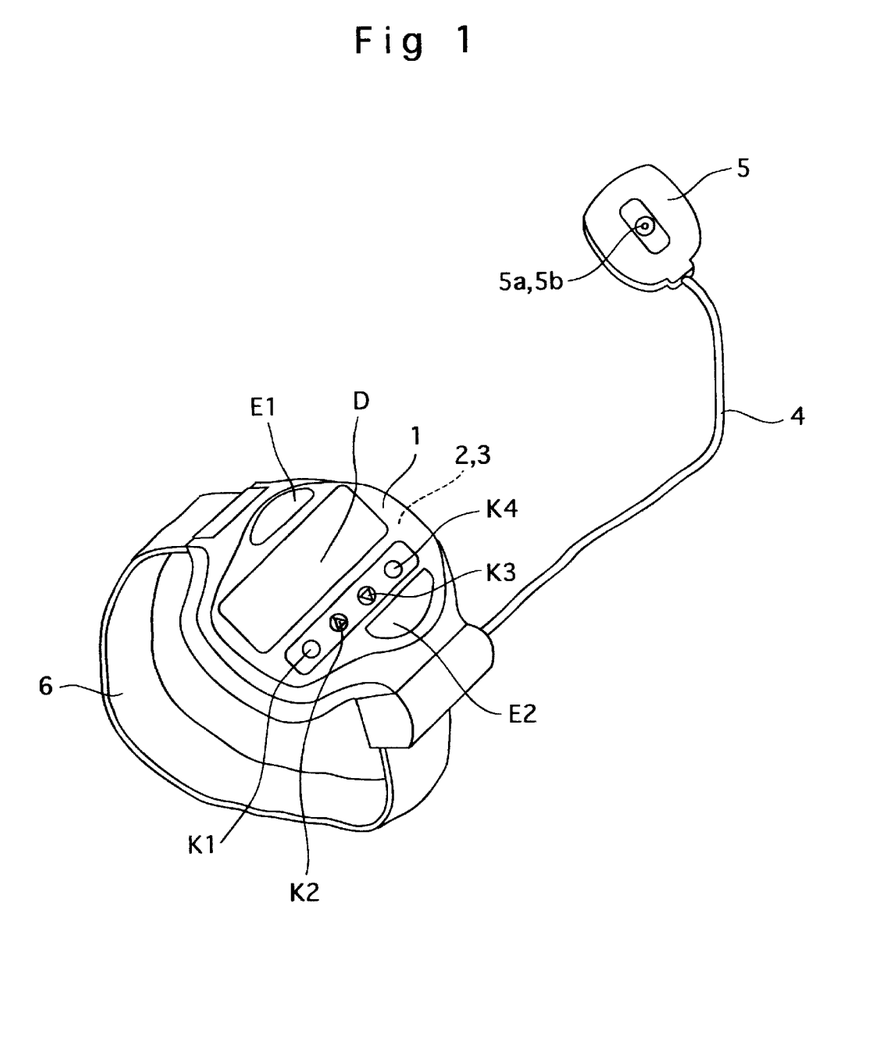
FIG. 1 is a perspective view of a calorie calculator according to the present invention.

Other objects and advantages of the present invention will be understood from the following description of a calorie calculator according to the present invention, which is shown in accompanying drawings:

Referring to FIG. 1, a calorie calculator according to the present invention has a bioelectric impedance measuring circuit 2, an acceleration meter 3, a momentum gauge (not shown) contained in a wristwatch-like casing 1, and a cardiac rate sensor 5 connected to the casing 1 via an associated wire 4. The wristwatch-like casing 1 has a wristband 6 fixed thereto, thus permitting a person to wear the calorie calculator by winding the wristband 6 around his wrist. The casing 1 may take any shape other than the wristwatch-like casing, and it may be a pedometer-like casing to be attached to one's band or a pendant-like object to be worn around the neck.

As shown in the drawing, the casing 1 has a liquid crystal display D, a measurement key K1, an up-counting key K2, a down-counting key K3, and a switching key K4 on its front, and is further provided with a feeding electrode E1 and a detecting electrode E2 on each side of the display D for measuring bioelectric impedances. Each electrode has one counter electrode E1 or E2 associated therewith. These counter electrodes are fixed to the rear side of the casing 1 or the rear side of the wristband 6, so that these counter electrodes may be put on the wrist when the calorie calculator is worn around the wrist.

Depression of the measurement key K1 starts the measurement of the body fat percentage and the calculation of the number of calories consumed in one's body. The up-counting key K2 allows the inputted figure to increase one for each depression whereas the down-counting key K3 allows the inputted figure to decrease one for each depression. The switching key K4 is used in selecting a desired mode of operation among measurement of the body fat percentage, measurement of the number of calories, the inputting of personal data, the setting of the goal at a desired body fat percentage and other menu items.

In inputting personal data such as the sex, age, height or weight, the display D shows a pre-selected sex and value to be corrected.

The display D is capable of showing the menu pertaining to the measurements of body fat percentage and the number of calories, the sex, the age, the height, the weight and other inputted data, and the results of such measurements. When no measurement is effected, the cardiac rate may be displayed on the display D all the time, or otherwise, the time may be displayed as a watch.

Figure 2:
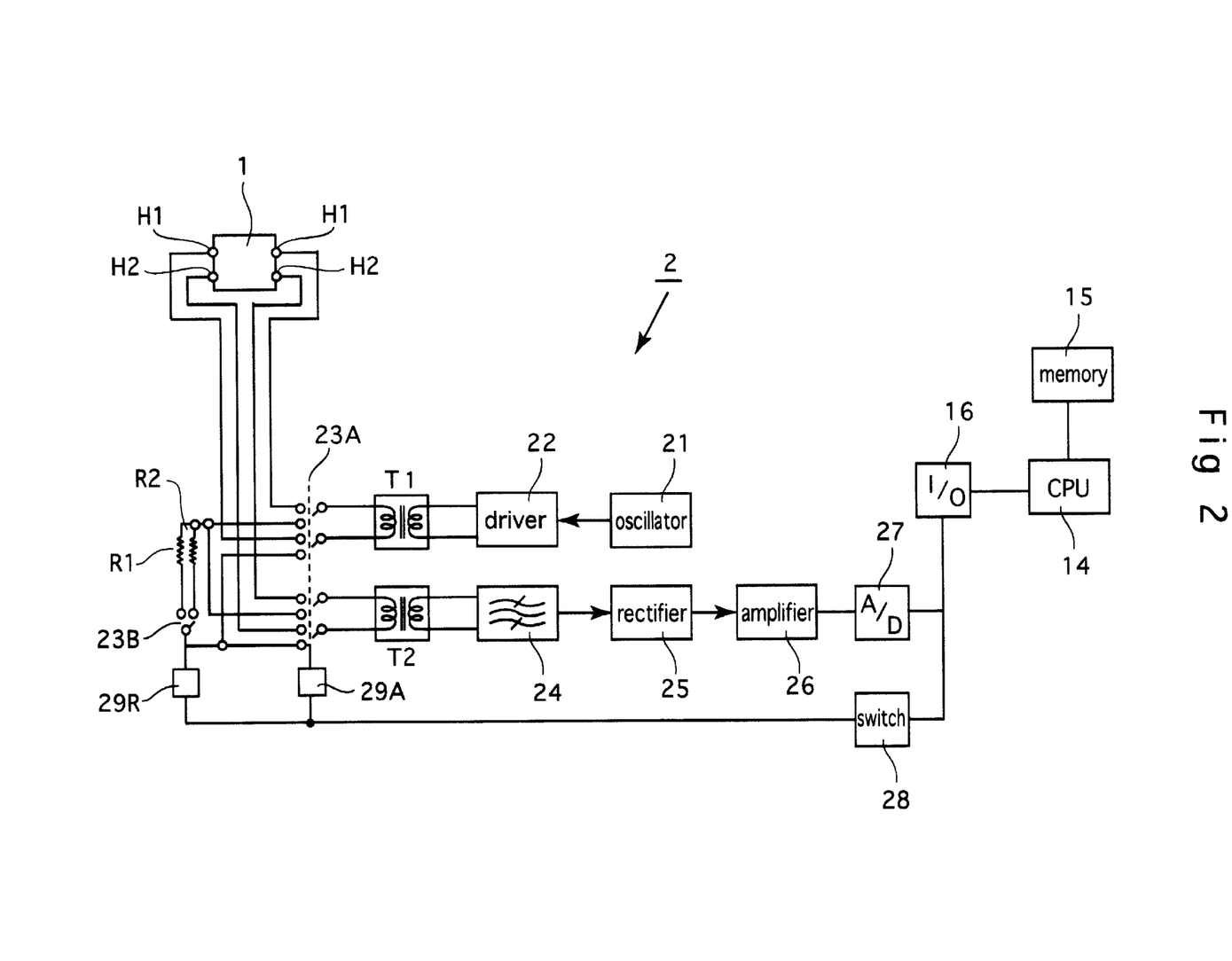
FIG. 2 shows a bioelectric impedance measuring circuit incorporated in the calorie calculator of FIG. 1.

Referring to FIG. 2, the bioelectric impedance measuring circuit 2 comprises a 50 KHz oscillator 21, a drive circuit 22 connected to the oscillator, a transformer T1 connected to the drive circuit 22, thus permitting the paired feeding electrodes E1 to be fed with sinusoidal signal of 50 KHz from the oscillator 21 via an associated switch 23A. As seen from FIG. 3, one's palm is put on the wristwatch-like casing 1 without allowing both hands to touch each other.

The biological impedance measuring circuit 2 further comprises a transformer T2, a band filter 24 connected to the transformer T2, a rectifier 25 connected to the band filter 24, an amplifier 26 connected to the rectifier 25, an analog-to-digital converter 27 connected to the amplifier 26, an interface 16 connected to the analog-to-digital converter 27 and a CPU 14 connected to the interface 16, thus permitting a signal representing the voltage appearing between the paired detecting electrodes E2 to be applied to the CPU 14 via the switch 23A Thus, the bioelectric impedance can be measured in terms of electric current flowing between the paired feeding electrodes E1 and the voltage appearing between the paired detecting electrodes E2.

With a view to eliminate any errors of parts for the bioelectric impedance measuring circuit 2 caused by temperature change and/or any variation with age the input-to-output characteristics of the impedance gauge need to be calibrated prior to measurement of biological impedance as follows: two variables, that is, bioelectric impedance and ac voltage appearing between the paired detecting electrodes are applied to an equation representing the impedance-and-detected ac voltage relation in the form of regression line, that is, $Z=kV+C_0$. Specifically two constants K and $C_0$ are determined by putting two known resistors R1 and R2 in circuit with the impedance gauge in place of the bioelectric impedance and by applying same voltage as used in determining the bioelectric impedance. The coefficient of regression K and the fixed constant $C_0$ are determined in terms of the ac voltages appearing across the resistors R1 and R2.

For this purpose a control signal is applied from the CPU 14 to the switch 23A through the I/O interface 16, the switching unit 28 and the switching control circuit 29A so that the switch 23A is made to turn and connect the secondary winding of the transformer T1 and the primary winding of the transformer T2 to the resistors R1, and then another control signal is applied to the switch 23B, allowing the switch 23B to turn and connect the secondary winding of the transformer T1 and the primary winding of the transformer T2 to the resistor R2.

Figure 4:
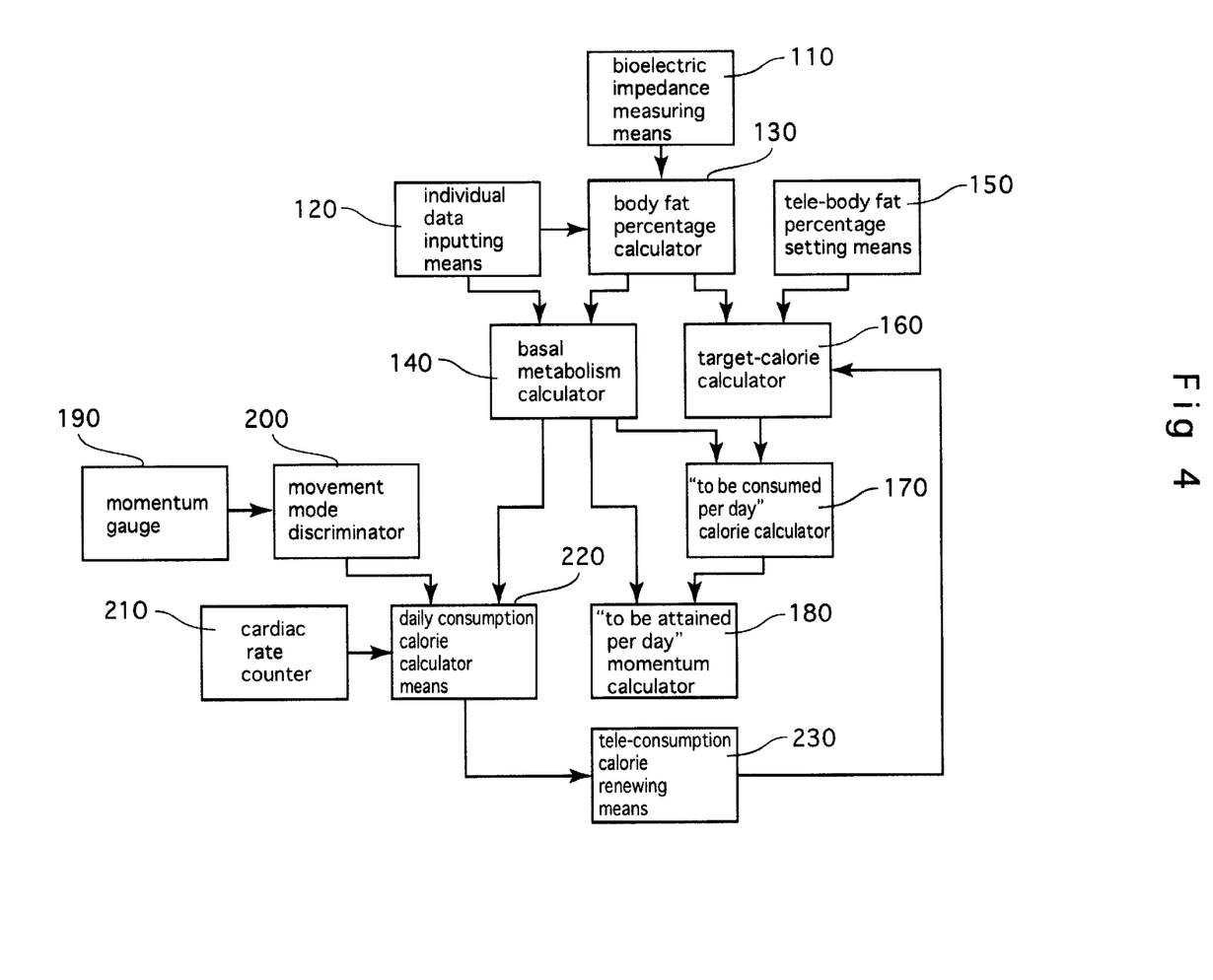
FIG. 4 is a block diagram showing the functions of the calorie calculator according to the present invention.

Referring to FIG. 4 the calorie calculator comprises: a bioelectric impedance measuring means 110 for determining the bioelectric impedance with the aid of the electrodes E1 and E2 of the wristwatch-like casing 1; an individual data inputting means 120 for inputting personal data such as sex, age, height and weight; a body fat percentage calculator means 130 for determining the body fat percentage on the basis of the bioelectric impedance and the personal data; a basal metabolism calculator means 140 for determining the quantity of basal metabolism on the basis of the personal data and the body fat percentage; a tele-body fat percentage setting means 150 for setting a goal at a desired body fat percentage; a target-calorie calculating means 160 for calculating the remaining number of calories to be consumed until arrival at the goal from the difference between the desired body fat percentage and the present body fat percentage; a "to be consumed per day" calorie calculating means 170 for calculating the number of calories to be consumed in a day, required for permitting one to reach one's goal; a "to be attained per day" momentum calculating means 180 for determining the daily momentum required for permitting one to reach one's goal; a momentum gauge 190 responsive to quickening (or body moving) and acceleration for determining the momentum of the body; a movement mode discriminator means 200 responsive to the quickening and acceleration for making a decision on what kind of movement is being effected; a cardiac rate counter means 210 for determining the count during movement; a daily consumption calorie calculator means 220 for calculating the total number of calories consumed per day by summing the number of calories consumed for each movement on the basis each of the basal metabolism, the movement mode, and the cardiac rate; and a tele-consumption calorie renewing means 230 for renewing the number of calories remaining on the way to the goal on the basis of the number of calories actually attained.

The basal metabolism calculator means 140 works according to the following equation:

the quantity of basal metabolism=$C_0$×weight×(100−body fat rate)/100+$C_1$

| | |
|---|---|
| $C_0$ = 24.0349 | for 40 or less year-old women |
| 21.951 | for 40 or more year-old women |
| 27.717 | for 40 or less year-old men |
| 25.333 | for 40 or more year-old men |
| $C_1$ = 427.64 | for 40 or less year-old women |
| 424.38 | for 40 or more year-old women |
| 188.21 | for 40 or less year-old men |
| 243.28 | for 40 or more year-old men |

No unit is applicable to $C_0$ and $C_1$

The tele-body fat percentage setting means 150 selects a desired figure in the recommendable range from 17 to 24 percent for women and from 14 to 20 percent for men. In case no selection is made, the tele-body fat percentage setting means 150 selects an appropriate figure for the user automatically.

The target-calorie calculating means 160 determines the number of calories to be consumed until arrival at the goal by determining the body fat amount to be reduced from the difference between the desired body fat percentage and the present body fat percentage and by estimating the number of calories required for reducing the so determined body fat amount at the converting rate of 7000 Kcal per body fat of 1 Kg:

the tele-consumption calorie (Kcal)=(present body fat percentage−tele-body fat percentage)×weight (Kg)×7000 (Kcal/Kg)/100.

The "to be consumed per day" calorie calculating means 170 determines the number of calories to be consumed each day, required for reaching the goal.

It may be realized that an appropriate number of calories consumed each day to attain the purpose of losing one's weight is 15% of the quantity of basal metabolism per day.

The "to be attained per day" momentum calculating means 180 calculates the momentum required per day for consuming the tele-consumption calorie per day. The momentum is given by the product of degree of active strength by movement time as follows:

the momentum (Kcal)=degree of active strength (Kcal/min.)× movement time (min.)

where the degree of active strength represents the number of calories consumed each minute, and is given by the following equation:

the degree of active strength (Kcal/min.)=(energy metabolism rate×basal metabolism+metabolism at rest or bed rest (Kcal)/ 1440 (min.)

Energy metabolism rate represents how many times of the quantity of basal metabolism the number of calories is consumed for a selected mode of movement or exercise, as for instance, follows: 2.0 times as many as the quantity of basal metabolism for walking for enjoyment; 3.0 times as many as the quantity of basal metabolism for walking; 5.0 times as many as the quantity of basal metabolism for quick walking; and 7.0 times as many as the quantity of basal metabolism for jogging. These figures were determined from actual practices. The quantity of metabolism at rest or bed rest is estimated to be 1.2 times as large as the quantity of basal metabolism.

Thus, the degree of active strength can be estimated as follows:

the degree of active strength for walking for enjoyment (Kcal/ min.)=(2.0×the quantity of basal metabolism+the quantity of metabolism at rest) (Kcal)/1440 (min.);

the degree of active strength for walking (Kcal/min.)=(3.0×the quantity of basal metabolism+the quantity of metabolism at rest) (Kcal)/1440 (min.);

the degree of active strength for quick walking (Kcal/min.)=(5.0× the quantity of basal metabolism+the quantity of metabolism at rest) (Kcal)/1440 (min.);

the degree of active strength for jogging (Kcal/min.)=(7.0×the quantity of basal metabolism+the quantity of metabolism at rest) (Kcal)/1440 (min.).

From the following equation, the length of time of a selected exercise required for consuming the amount of momentum remaining on the way to the goal can be estimated.

the length of time involved for taking a selected exercise a day (min.)=the number of calories consumed a day (Kcal)/the degree of active strength for the exercise The result is given as for example, follows: 50 minute-long walking and 30 minute-long jogging. A minimum length of time involved for starting the burning of body fat is 12 or more minutes long, which minimum period must be expired prior to required counting.

The momentum gauge means 190 detects a three-axial movement from the signals from the associated quickening-and-acceleration meter 3 for determining the quickening and the acceleration of movement.

The momentum gauge uses a pendulum having a magnet attached thereto. The pendulum is responsive to the moves of the body for swinging in three axial directions, thereby causing an associated switching means to turn on and off, counting how many times the body moves. The move of the body will increase its pitch and amplitude with the increase of quickness in movement. The acceleration meter 3 is used in identifying the movement mode in terms of quickness in movement, such as ramble or jogging.

Figure 5:
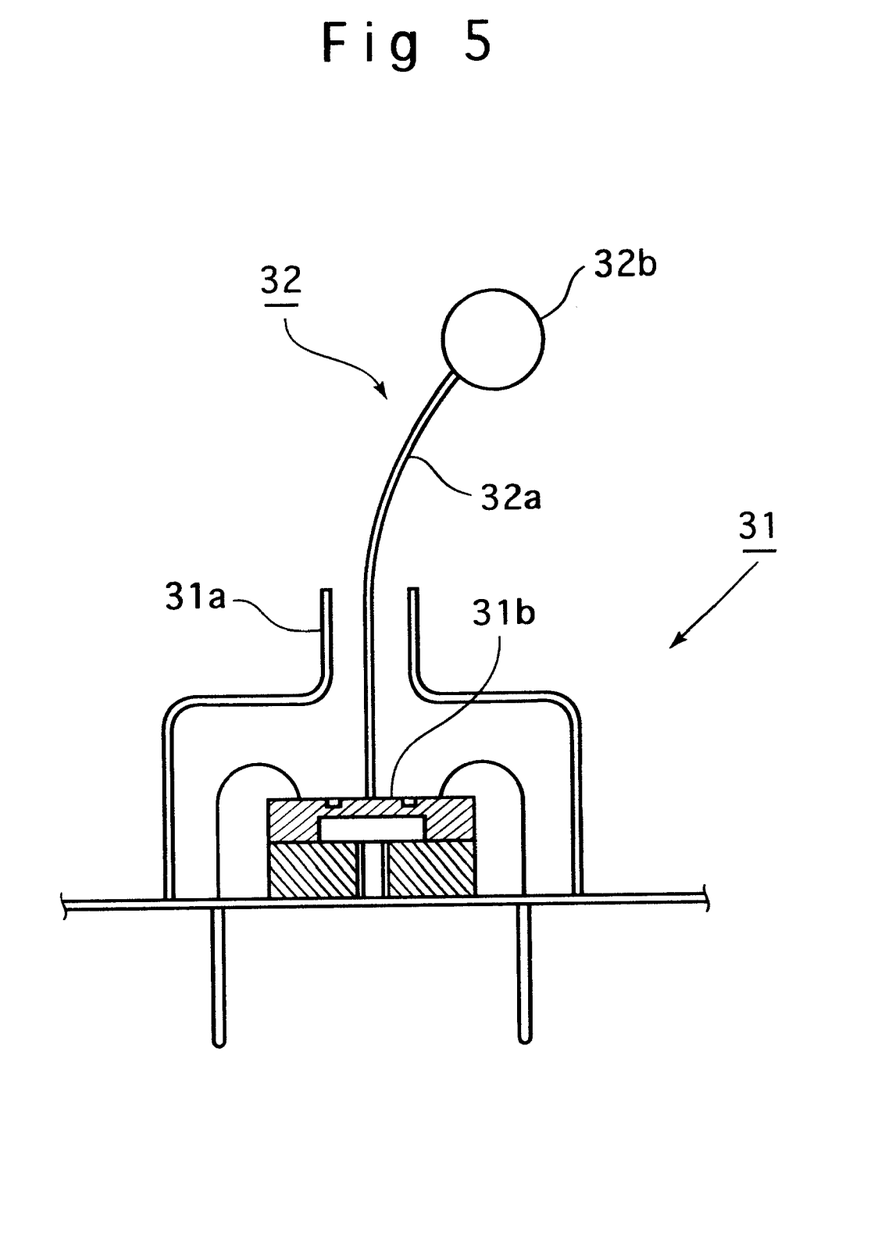
FIG. 5 is a longitudinal section showing an acceleration meter incorporated in the calorie calculator of FIG. 1.

FIG. 5 illustrates an acceleration meter 3 comprising a semiconductor pressure sensor 31 and a swingable pendulum 32 inserted in the port 31a of the sensor housing. Specifically, the pendulum 32 comprises a flexible wire 32a having a weight 32b fixed to its top, and the wire 32a is fixed at its bottom end to the silicone diaphragm 31b. In operation the weight 32b swings in all directions, the movements of which are transmitted to the silicone diaphragm 31b via the wire 32a, thereby causing the silicone diaphragm 31b to be deformed and stressed Thus, the strain gauge in the form of silicone diaphragm 31b causes the piezo-resistance effect, varying its resistance to generate a bridge voltage representing the degree of acceleration. The bridge voltage is amplified in an associated high-gain amplifier to determine the degree of acceleration. There are a variety of acceleration meters as for instance follows: a weight is connected to an associated spring to detect the relative displacement of the weight in terms of the strain appearing in the spring; a weight is connected to an associated piezo-electric element capable of producing electrons whose amount is proportional to the displacement of the weight; or a weight has a coil fixed thereto, and is adapted to move in the magnetic field, thereby permitting determination of acceleration in terms of the electromotive force induced in the coil when the weight moves across the magnetic field.

The movement mode discriminator means 200 identifies in which movement mode the wearer is moving in terms of the count of the quickening gauge and the voltage appearing at the acceleration meter 3. There are four different movement modes to be discriminated, walking for enjoyment, quick walking, jogging, and running. Even if the accelerator 3 provides a signal at its output terminal when the wearer is riding on a vehicle, the quickening gauge remains dormant, permitting the movement mode discriminator means to make a decision of the wearer being still, thus preventing calculation of the number of calories in motionless condition.

The cardiac rate meter 210 uses a cardiac rate sensor 5 for determining the cardiac rate in movement exclusively. The cardiac rate sensor 5 makes use of infrared light being absorbed by hemoglobin in the blood in blood capillaries of fingertips, and of the blood concentration varying with the cardiac rate. The cardiac rate sensor 5 is fixedly applied to a selected fingertip with the aid of an associated holder 7, thereby permitting the infrared light from an infrared light source 5a to be detected continuously, and then, the so detected infrared light is converted to electric signal for counting the cardiac rate.

The cardiac sensor 5 may be applied to an ear lobe like a clip. Otherwise, an electroded transmitter (not shown in the drawings) may be applied to the breast to detect appearance of voltage around the heart every time it pulses, thus counting the pulsation of the heart and sending a wireless signal representing the cardiac rate to a receiver (not shown in the drawings) in the casing 1.

The daily consumption calorie calculator means 220 sums the numbers of calories consumed by different movements taken in a day, thereby calculating the total number of calorie consumed per day. The number of calories consumed for each movement is equal to the momentum above described, and the number of calories consumed in a day can be obtained from the following equation:

the number of calories consumed in a day (Kcal)=Σ{degree of active strength (Kcal/min.)×movement time (min.)} the degree of active strength (Kcal/min.)=energy metabolism rate× quantity of basal metabolism+quantity of metabolism at rest (Kcal)/1440 (min.)

Figure 6:
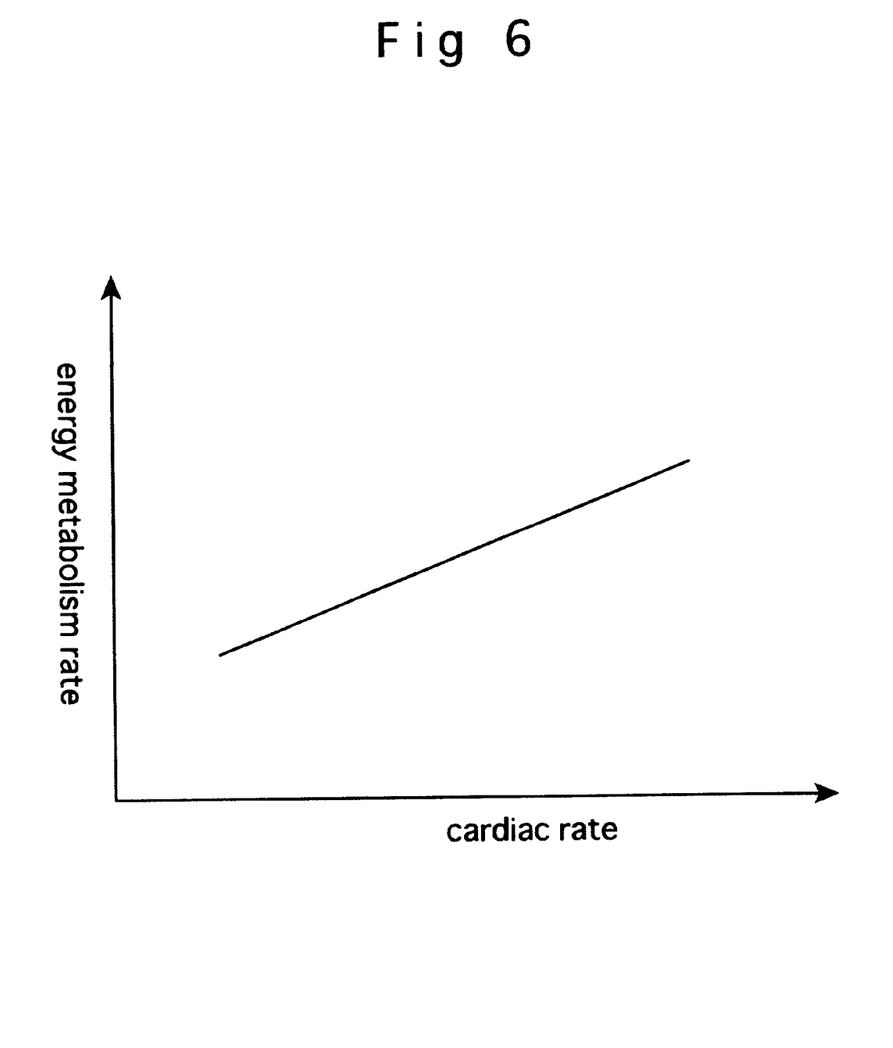
FIG. 6 shows how the energy metabolism varies with the cardiac rate.

As seen from FIG. 6, the energy metabolism rate (ordinate) is closely related with the cardiac rate (abscissa), and the energy metabolism rate can be determined from a regression equation, which is given in terms of the two variables. The energy metabolism rate is proportional with the acceleration in movement, but the energy metabolism rate cannot be determined correctly in terms of acceleration because no modification with loading such as experienced in climbing the slope can be effected. Therefore, the energy metabolism rate is determined in terms of the cardiac rate rather than the acceleration.

The degree of active strength at which the body fat can be burnt effectively is found when the cardiac rate is approximately 60 to 90% of the maximum cardiac rate, and therefore, the numbers of calories consumed while the cardiac rate remain in the 60-to-90 percent range are summarized a day to provide a daily calorie-consumption. The maximum cardiac rate for men is equal to (220−Age) whereas the maximum cardiac rate for women is equal to (210−Age). In case of ages below 20, the age in either equation is 20.

To improve the accuracy with which the energy metabolism can be estimated an appropriate regression equation is used for each different mode of movement because the relation between the energy metabolism and the cardiac rate is dependent on the mode of movement.

It is therefore necessary that a decision be made on what mode of movement is taken prior to the calculation of momentum. An appropriate regression equation is selected for the mode of movement, which is identified by the movement mode discriminator means 200. Then, the energy metabolism is determined from the so selected regression equation and the cardiac rate, which is determined by the cardiac meter 210. Such regression equations can be obtained by using a treadmill capable of progressively increasing load with which one is loaded.

The tele-consumption calorie renewing means 230 renews the number of calories remaining on the way to the goal by subtracting the number of calories actually consumed in a day from the last renewed number of calories. Every time the body fat percentage has been renewed, the target number of calories is renewed, too.

In determining the body fat percentage, first, some personal data, that is, the sex, age, height and weight are inputted with the aid of the switching key K4, the up-counting key K2 and the down-counting key K3. Such inputting is unnecessary if the personal data remains unchanged.

Figure 3:
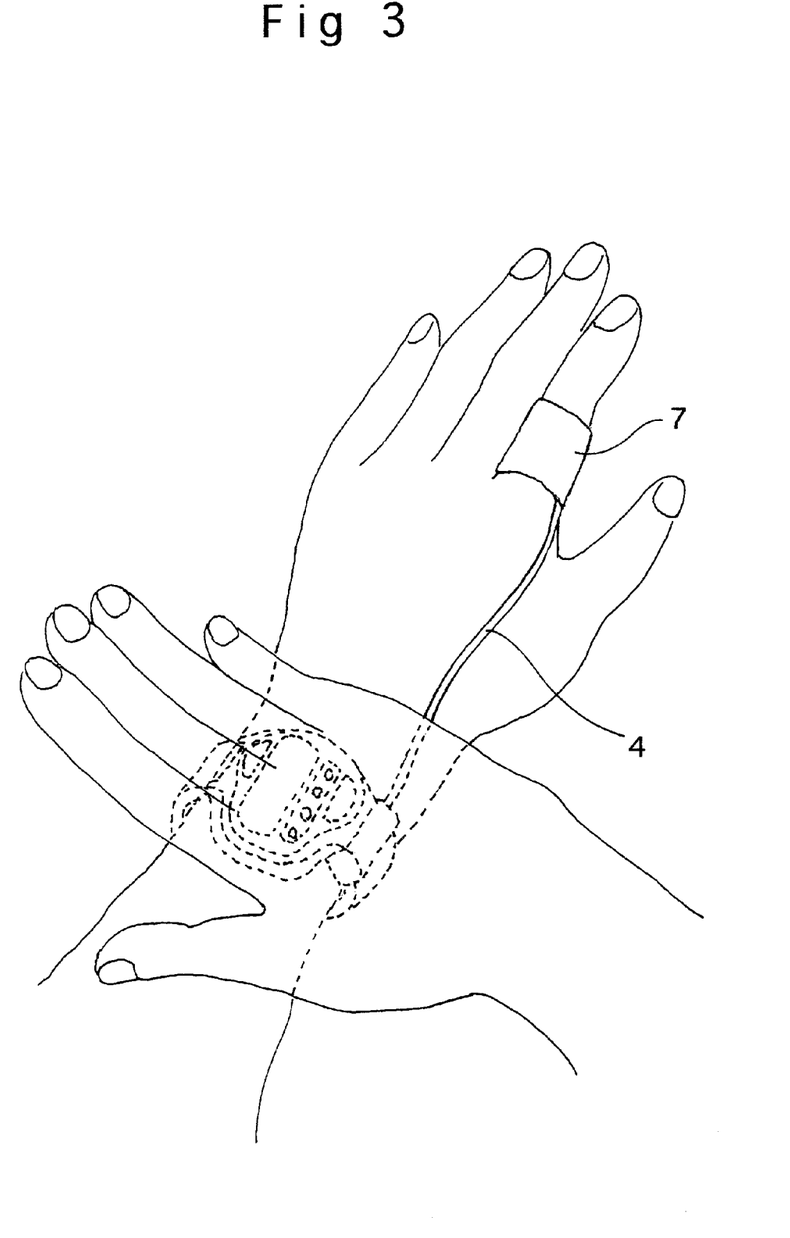
FIG. 3 illustrates how the calorie calculator is used.

Then, the casing 1 is worn around the wrist of one hand, and the palm of the other hand is put on the electrodes of the surface of the casing 1, starting measurement of the body fat percentage by depressing the measurement key K1.

After a while the body fat percentage is shown on the display D. When setting the goal at a desired body fat percentage, the switching key K4 is depressed to change the operation mode, selecting a desired body fat percentage among those listed in the table. If no selection is made, an appropriate body fat percentage will be automatically set as a target value.

When it is desired that the total number of calories consumed in a day is determined, the switching key K4 is depressed to change the operation mode, and then, the measurement key K1 is depressed to start the required measurement.

When measurement of the number of calories starts, the display D shows the cardiac rate, the tele-consumption calorie required for attaining the tele-body fat percentage, the total number of calories consumed each day, the required exercise time per day, which is determined for a selected movement mode. The tele-consumption calorie is renewed and set as an initial value every time the body fat percentage is measured, or another desired body fat percentage is selected. Usually the tele-consumption calorie is renewed by subtracting the number of calories actually consumed each day.

INDUSTRIAL APPLICABILITY

As may be understood from the above, a calorie calculator according to the present invention calculates the total number of calories consumed each day on the basis of the momentum, the cardiac rate and the quantity of basal metabolism. The precision with which the number of calories can be calculated is significantly improved by taking the quantity of individual basal metabolism into account.

The calorie calculator permits the setting of tele-body fat percentage; the determining of number of calories to be consumed for attaining such target value of body fat percentage; and the renewing of the tele-consumption calorie in response to the actual consumption of total number of calories per day. Thus, the user can be visually informed each day of how far he is on the way to the goal thus encouraging him all the time until he has reached the goal.

Also, the calorie calculator permits the setting of tele-body fat percentage and the determining of momentum required for attaining such target. The user can be visually informed of how long the selected mode of movement should be continued each day, thus permitting him to control the daily momentum.

Finally the calorie calculator measures the momentum both with a quickening gauge capable of counting three-axial movements and an acceleration meter capable of determining accelerations along the three axial directions, thereby detecting movements in all directions. Thus, the total amount of daily movement can be estimated with precision. Combination of the quickening gauge and the acceleration meter effectively prevents the erroneous determination of momentum which otherwise, would be caused if the user takes a vehicle.

What is claimed is:

1. A calorie calculator comprising: a housing having a display equipped therewith, said housing being wearable to a selected part of one's body; electrodes attached to the surface of the housing for determining bioelectric impedance; momentum gauge means responsive to three-dimensional body movements for determining the momentum of a wearer; cardiac rate measuring means; individual data inputting means for inputting the sex, age, height, weight and other personal data; body fat percentage calculator means for determining the body fat percentage of the wearer from the bioelectric impedance and personal data; basal metabolism calculator means for determining the quantity of basal metabolism of the wearer from the body fat percentage and the personal data of the wearer; and calorie calculator means for calculating the total number of calories consumed a day from the momentum, cardiac rate and quantity of basal metabolism of the wearer, whereby at least the body fat percentage and the total number of calories consumed a day are given on the display.

2. A calorie calculator according to claim 1, wherein said momentum gauge means responsive to three-dimensional movements for determining the momentum of a wearer may comprise a quickening gauge for counting moves of the body in three axial directions and for determining the momentum in terms of counts.

3. A calorie calculator according to claim 1, wherein said momentum gauge means responsive to three-dimensional movements for determining the momentum of a wearer may comprise an acceleration gauge for determining the momentum in terms of detected accelerations in three axial directions.

4. A calorie calculator according to claim 1, wherein said momentum gauge means responsive to three-dimensional movements for determining the momentum of a wearer may comprise a quickening gauge for counting moves of the body in three axial directions, and an acceleration gauge for determining accelerations in three axial directions, whereby the momentum may be determined in terms of counts and accelerations.

5. A calorie calculator comprising: a housing having a display equipped therewith, said housing being wearable to a selected part of one's body; electrodes attached to the surface of the housing for determining bioelectric impedance; momentum gauge means responsive to three-dimensional body movements for determining the momentum of a wearer; cardiac rate measuring means; individual data inputting means for inputting the sex, age, height, weight and other personal data; body fat percentage calculator means for determining the body fat percentage of the wearer from the bioelectric impedance and personal data; basal metabolism calculator means for determining the quantity of basal metabolism of the wearer from the body fat percentage and personal data of the wearer; tele-body fat percentage setting means for setting the goal at a desired body fat percentage; tele-consumption calorie calculator means for determining the number of calories required for reaching the goal of desired body fat percentage; and calorie calculator means for calculating the total number of calories consumed a day from the momentum, cardiac rate and quantity of basal metabolism of the wearer, whereby at least the body fat percentage, the number of calories required for reaching the goal, and the total number of calories consumed a day are given on the display.

6. A calorie calculator according to claim 5, wherein said momentum gauge means responsive to three-dimensional movements for determining the momentum of a wearer may comprise a quickening gauge for counting moves of the body in three axial directions and for determining the momentum in terms of counts.

7. A calorie calculator according to claim 5, wherein said momentum gauge means responsive to three-dimensional movements for determining the momentum of a wearer may comprise an acceleration gauge for determining the momentum in terms of detected accelerations in three axial directions.

8. A calorie calculator according to claim 5, wherein said momentum gauge means responsive to three-dimensional movements for determining the momentum of a wearer may comprise a quickening gauge for counting moves of the body in three axial directions, and an acceleration gauge for determining accelerations in three axial directions, whereby the momentum may be determined in terms of counts and accelerations.

9. A calorie calculator comprising: a housing having a display equipped therewith, said housing being wearable to a selected part of one's body; electrodes attached to the surface of the housing for determining bioelectric impedance; momentum gauge means responsive to three-dimensional body movements for determining the momentum of a wearer; cardiac rate measuring means; individual data inputting means for inputting the sex, age, height, weight and other personal data; body fat percentage calculator means for determining the body fat percentage of the wearer from the bioelectric impedance and the personal data; basal metabolism calculator means for determining the quantity of basal metabolism of the wearer from the body fat percentage and personal data of the wearer; tele-body fat percentage setting means for setting a goal at a desired body fat percentage; momentum calculator means for determining the momentum required for reaching the goal of desired body fat percentage; and calorie calculator means for calculating the total number of calories consumed a day from the momentum, cardiac rate and quantity of basal metabolism, whereby at least the measured data, the body fat percentage, the required momentum, and the total number of calories consumed a day are given on the display.

10. A calorie calculator according to claim 9, wherein said momentum gauge means responsive to three-dimensional movements for determining the momentum of a wearer may comprise a quickening gauge for counting moves of the body in three axial directions and for determining the momentum in terms of counts.

11. A calorie calculator according to claim 9, wherein said momentum gauge means responsive to three-dimensional movements for determining the momentum of a wearer may comprise an acceleration gauge for determining the momentum in terms of detected accelerations in three axial directions.

12. A calorie calculator according to claim 9, wherein said momentum gauge means responsive to three-dimensional movements for determining the momentum of a wearer may comprise a quickening gauge for counting moves of the body in three axial directions, and an acceleration gauge for determining accelerations in three axial directions, whereby the momentum may be determined in terms of counts and accelerations.

13. A calorie calculator comprising: a housing having a display equipped therewith, said housing being wearable to a selected part of one's body; electrodes attached to the surface of the housing for determining the bioelectric impedance of a wearer; momentum gauge means responsive to three-dimensional body movements for determining the momentum of the wearer; cardiac rate measuring means; individual data inputting means for inputting the sex, age, height, weight and other personal data; body fat percentage calculator means for determining the body fat percentage of the wearer from the bioelectric impedance and the personal data; basal metabolism calculator means for determining the quantity of basal metabolism of the wearer from the body fat percentage and personal data of the wearer; tele-body fat percentage setting means for setting a goal at a desired body fat percentage; tele-consumption calorie calculator means for determining the number of calories to be consumed until arrival at the goal of desired body fat percentage; calorie calculator means for calculating the total number of calories a day from the momentum, cardiac rate and quantity of basal metabolism; and tele-consumption calorie renewing means for renewing the number of calories required for reaching the goal in consideration of the loss of the total number of calories consumed per day, whereby at least the measured data and the number of required calories renewed by the tele-consumption calorie renewing means are given on the display along with the body fat percentage.

14. A calorie calculator according to claim 13, wherein said momentum gauge means responsive to three-dimensional movements for determining the momentum of a wearer may comprise a quickening gauge for counting moves of the body in three axial directions and for determining the momentum in terms of counts.

15. A calorie calculator according to claim 13, wherein said momentum gauge means responsive to three-dimensional movements for determining the momentum of a wearer may comprise an acceleration gauge for determining the momentum in terms of detected accelerations in three axial directions.

16. A calorie calculator according to claim 13, wherein said momentum gauge means responsive to three-dimensional movements for determining the momentum of a wearer may comprise a quickening gauge for counting moves of the body in three axial directions, and an acceleration gauge for determining accelerations in three axial directions, whereby the momentum may be determined in terms of counts and accelerations.

* * * * *